United States Patent [19]

Lantzsch et al.

[11] Patent Number: 4,845,288

[45] Date of Patent: Jul. 4, 1989

[54] PROCESS FOR THE PREPARATION OF HYDROXYBENZALDOXIME O-ETHERS

[75] Inventors: Reinhard Lantzsch, Wuppertal; Heinz Ziemann, Leichlingen; Hans-Ludwig Elbe, Wuppertal, all of Fed. Rep. of Germany

[73] Assignee: Bayer Aktiengesellschaft, Leverkusen, Fed. Rep. of Germany

[21] Appl. No.: 147,417

[22] Filed: Jan. 25, 1988

[30] Foreign Application Priority Data

Feb. 4, 1987 [DE] Fed. Rep. of Germany ....... 3703236

[51] Int. Cl.$^4$ ............................................ C07C 131/00
[52] U.S. Cl. ..................................... 564/256; 534/565
[58] Field of Search ................. 564/256, 422; 534/565

[56] References Cited

U.S. PATENT DOCUMENTS

| | | | |
|---|---|---|---|
| 4,612,394 | 9/1986 | Kotera et al. ...................... | 564/422 |
| 4,739,119 | 4/1988 | Elbe et al. ......................... | 564/256 |

FOREIGN PATENT DOCUMENTS

| | | | |
|---|---|---|---|
| 54809 | 6/1982 | European Pat. Off. ............ | 564/422 |
| 3534731 | 4/1987 | Fed. Rep. of Germany ...... | 564/256 |

OTHER PUBLICATIONS

T. Satoh et al., "Selective Reduction of Aromatic Nitro Compounds with . . . .," Chem. Pharm. Bull., vol. 29, (1981) pp. 2443–2445.

Houben–Weyl, "Methoden der Organischen Chemie", V. VI/1c, pp. 247–249.

Ried und Lotterhos, "Über heterocyclisch substituierte Aminosäuren . . .", Chem. Ber. 88, (1955) pp. 38–41.

Niederl and Smith, "Synthesis of Long Chain Substituted Isocyclics and . . . ", J. Amer. Chem. Soc. 59 (1937) pp. 715–717.

Jones and Major, "Catalytic Reduction of O–Alkyl Substituted Oximes", J. Amer. Chem. Soc. 52 (1930) pp. 669–679.

*Primary Examiner*—James H. Reamer
*Attorney, Agent, or Firm*—Sprung Horn Kramer & Woods

[57] ABSTRACT

A process for the preparation of a hydroxybenzaldoxime O-ether of the formula

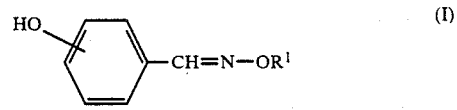

(I)

in which $R^1$ represents alkyl, comprising (a) in a first step, hydrogenating a nitro-benzaldoxime O-ether of the formula

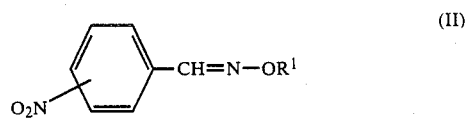

(II)

using the calculated amount of hydrogen in the presence of a catalyst and in the presence of a diluent, and (b) in a second step, reacting the amino-benzaldoxime O-ether of the formula

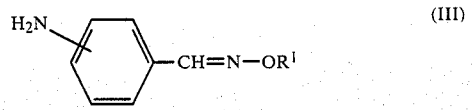

(III)

thus obtained with a diazotizing agent in acidic, aqueous solution, and, without isolation, thermally hydrolyzing the resultant diazonium salt of the formula

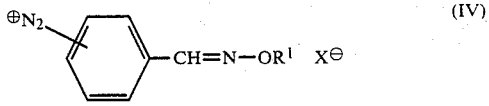

(IV)

in which $X^\ominus$ represents an equivalent of an inorganic anion, in acidic, aqueous solution.

10 Claims, No Drawings

PROCESS FOR THE PREPARATION OF HYDROXYBENZALDOXIME O-ETHERS

The invention relates to a new process for the preparation of known hydroxybenzaldoxime O-ethers, which can be used as intermediates for the synthesis of compounds having a fungicidal, insecticidal and antimycotic activity.

It has already been disclosed that certain hydroxybenzaldoxime O-ethers can be prepared by reacting hydroxybenzaldehydes with the appropriate hydroxylamine derivatives (cf. EP-OS (European Published Specification) No. 0,076,370 and EP-OS (European Published Specification) No. 0,115,828). The reaction concerned can be illustrated by the following equation:

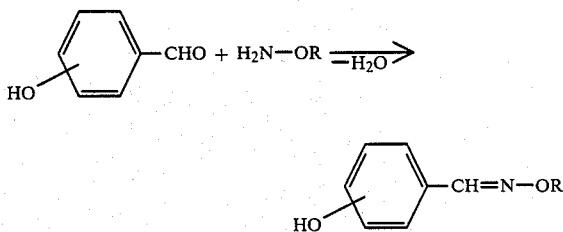

R = alkyl, alkenyl or alkinyl.

However, it is disadvantageous in this process that the starting materials are only available through a complicated synthesis. They are therefore relatively expensive and their use for preparation of hydroxybenzaldoxime O-ethers on an industrial scale is problematic. In addition, the yields of hydroxy-benzaldoxime O-ethers in the abovementioned process are not always satisfactory.

It has now been found that known hydroxy-benzaldoxime O-ethers of the formula

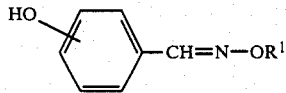

in which $R^1$ represents alkyl,
are obtained when (a) in a first step, nitro-benzaldoxime O-ethers of the formula

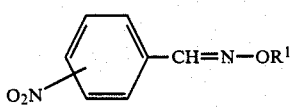

in which $R^1$ has the abovementioned meaning,
are hydrogenated using the calculated amount of hydrogen in the presence of a catalyst and in the presence of a diluent, and (b) in a second step, the amino-benzaldoxime O-ethers of
the formula

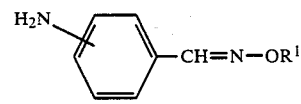

in which $R^1$ has the abovementioned meaning,
thus obtained are reacted with a diazotizing agent in acidic, aqueous solution, and the resultant diazonium salts of the formula

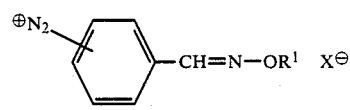

in which $X^\ominus$ represents an equivalent of an inorganic anion, and $R^1$ has the abovementioned meaning,
are thermally hydrolyzed in acidic, aqueous solution without intermediate isolation.

It is extremely surprising that the reaction according to the invention proceeds smoothly and in good yield under the process conditions specified. Based on the known prior art, it was to be expected that the C=N double bond present in the compounds of the formula (II) would be saturated to a noticeable extent in the hydrogenation in the first step of the process according to the invention, since hydrogenations of such double bonds occur very easily (cf. Chem. Ber. 88, 38 (1955); J. Amer. Chem. Soc. 59, 716 (1937) and J. Amer. Chem. Soc. 52, 669 (1930)). Under certain circumstances, even reduction to the amine or hydrogenolysis to the methyl group occurs.

It is furthermore known that oximes can be converted into aldehydes by reducing agents in the presence of Raney nickel (cf. Chem. Comm. 16, 803 (1986)). It was therefore to be presumed that this type of hydrogenolytic cleavage would also occur under the reaction conditions in the first step of the process according to the invention. In addition, it was to be feared that hydrolysis of the oxime ether through the water produced during the reduction of the nitro group would lead to formation of an aldehyde. Surprisingly, however, these interfering side reactions were not observed in the case of the process according to the invention. In addition, it could also not be presumed that, in the second step of the process according to the invention, the reactive carbo-cation (on the aromatic ring) produced on the thermal hydrolysis of the diazonium salt would react selectively in the desired fashion, and that intermolecular attack at the free electron pair of the oxime either nitrogen would not occur.

The process according to the invention is distinguished by a number of advantages. Thus, it permits the preparation of hydroxy-benzaldoxime O-ethers of the formula (I) in high yields, inexpensive and readily available compounds being employed as starting materials. Furthermore, the reaction is simple to carry out and isolation of the benzaldoxime O-ethers of the formula (I) presents no difficulties. The process according to the invention is therefore particularly suitable for preparation of hydroxy-benzaldoxime O-ethers of the formula (I) on an industrial scale.

If 4-nitro-benzaldoxime O-methyl ether is used as starting material, hydrogen as hydrogenation agent, Raney nickel as catalyst, aqueous sulphuric acid as acidic medium and sodium nitrite as diazotizing agent, the course of the process according to the invention may be illustrated by the following equation:

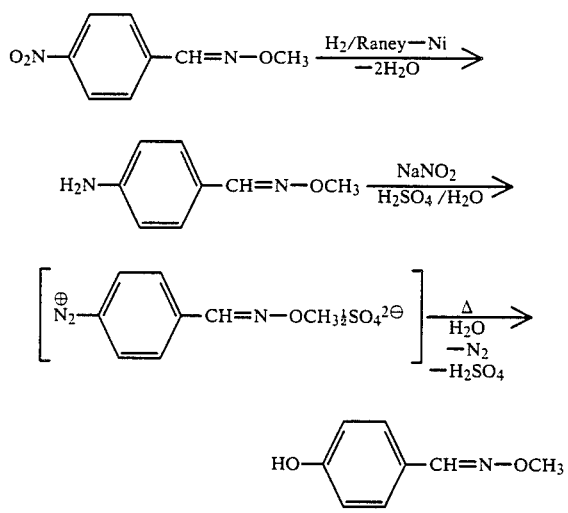

Formula (II) provides a general definition of the nitro-benzaldoxime O-ethers required as starting materials in the process according to the invention. In this formula, $R^1$ preferably represents straight-chain or branched alkyl having 1 to 20 carbon atoms.

Particularly preferred starting materials are those nitro-benzaldoxmime O-ethers of the formula (II) in which $R^1$ represents straight-chain or branched alkyl having 1 to 10 carbon atoms.

Very particularly preferred starting materials are those nitro-benzaldoxime O-ethers of the formula (II) in which $R^1$ represents straight-chain or branched alkyl having 1 to 4 carbon atoms, the 4-nitro-benzaldoxime O-ethers in each case being of particular interest.

The nitro-benzaldoxime O-ethers of the formula (II) are known or can be prepared in a simple fashion by known processes (cf. Ber. 24, 2548 (1891)).

In the first step of the process according to the invention, hydrogen is used as the hydrogenation agent. In this step, the hydrogen pressure can vary within a relatively wide range. In general, the reaction is carried out under a hydrogen pressure between 1 and 50 bar, preferably between 2 and 20 bar, in particular between 3 and 10 bar.

Suitable catalysts when carrying out the first step of the process according to the invention are preferably nickel-containing catalysts, such as, for example, Raney nickel, Raney nickel/iron, Raney nickel/copper or nicklel on silicon dioxide.

Possible diluents when carrying out the first step of the process according to the invention are all inert organic solvents which are conventional for such reactions. Ethers, such as diethyl ether, dioxane or tetrahydrofuran, furthermore alcohols, such as methanol, ethanol or isopropanol, and in addition aliphatic, cycloaliphatic or aromatic hydrocarbons, such as pentane, hexane, petroleum ether, cyclohexane, methylcyclohexane, benzene, toluent or xylene, furthermore esters and amides, such as, for example, dimethylformamide, may preferably by used.

The reaction temperatures may be varied within a certain range when carrying out the first step of the process according to the invention. In general, the first step is carried out at temperatures between 0° C. and 150° C., preferably between 5° C. and 50° C., in particular between 10° and 30° C.

Suitable diazotizing agents when carrying out the second step of the process according to the invention are all components which are conveniently suitable for a diazotization. Sodium nitrite, potassium nitrite, ammonium nitrite and nitrosylsulphuric acid may preferably be used.

The reaction in the second step of the process according to the invention is carried out in acidic, aqueous solution. Suitable acids are preferably inorganic acids. Sulphuric acid may particularly preferably be used. Accordingly, $X^\ominus$ in the case of the diazonium salts of the formula (IV) represents an equivalent of an anion of the inorganic acid used. $X^\ominus$ preferably represents an equivalent of a sulphate anion.

In the diazotization, the concentration of acid may be varied within a relatively wide range. In general, solutions are used in which the acid concentration is between 1 and 50% by weight, preferably between 1 and 30% by weight.

The reaction temperatures may also be varied within a certain range when carrying out the second step of the process according to the invention. The diazotization is generally carried out at temperatures between 0° and 20° C., preferably between 0° and 10° C.

The subsequent thermal hydrolysis of the diazonium salts is generally carried out at temperatures between 50° and 100° C., preferably between 70° and 100° C.

When carrying out the first step of the process according to the invention, the nitrogenzaldoxime O-ether of the formula (II) is reacted with a calculated amount of hydrogen in the presence of a catalyst.

When carrying out the second step of the process according to the invention, 1 to 1.5 mols, preferably 1 to 1.2 mols, of diaotizing agent are generally employed per mole of aminobenzaldoxime O-ether of the formula (II). The excess diazotizing agent can be destroyed in a conventional fashion before the thermal hydrolysis by adding urea.

In a particular embodiment of the second step of the process according to the invention, the diazonium salt solution is metered into aqueous sulphuric acid at 50° to 100° C., preferably at 70° to 100° C., for thermal hydrolysis, the concentration of sulphuric acid being 1 to 50% by weight, preferably 1 to 30% by weight. The metering-in rate here is selected so that the temperature of the initially introduced aqueous sulhpuric acid can be kept constant.

In detail, a procedure is followed when carrying out the first step of the process according to the invention in which nitro-benzaldoxime O-ether, catalyst and diluent are introduced into a pressure vessel, and hydrogen is then pumped in until the theoretically required amount has been taken up. Work-up is then effected by filtering off the catalyst, evaporating the filtrate under reduced pressure, and, if necessary, purifying the product remaining by distillation. When carrying out the second step of the process according to the invention, a procedure is generally followed in which amino-benzaldoxime O-ether is slurried in dilute, aqueous acid, the reaction mixture is cooled, the diazotizing agent is added, and, when the reaction is complete, any diazotizing agent still present is destroyed, if necessary, by adding urea. For the subsequent thermal hydrolysis, the diazonium salt solution is introduced into warmed acid and stirred for a few minutes. The final products are isolated by conventional methods. In general, a procedure is followed in which the reaction mixture is cooled to room temperature, the pH is adjusted to the alkaline region by adding base, the product is extracted repeatedly with a sparingly water-soluble organic solvent, the combined organic phases are evaporated under reduced pressure, if appropriate after prior drying, and the product remaining is distilled under reduced pressure.

The hydroxy-benzaldoxime O-ethers of the formula (I) which can be prepared by the process according to the invention are generally valuable starting materials for the synthesis of biologically active compounds. Thus, they can be used, for example, for the synthesis of oxime ethers which have good insecticidal properties (cf. EP-OS (European Published Specification) No. 0,115,828); azolylphenoxy derivates which have excellent fungicidal properties (cf. EP-OS (European Published Specification) No. 0,076,370); 1-hydroxyethyl-triazolyl derivatives which have good fungicidal and antimycotic properties (cf. EP-OS (European Published Specification) No. 0,110,048 and DE-OS (German Published Specification) No. 3,314,548); and hydroxyalkylazolyl derivatives which have good antimycotic activity (cf. DE-OS (German Published Specification) No. 3,427,844).

Thus, for example, 3,3-dimethyl-1-(4-methoximinomethyl-phenoxy)-1-(1,2,4-triazol-1-yl)-butan-2-one of the formula

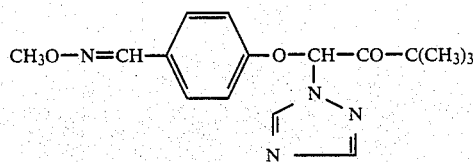

can be prepared by reacting 3,3-dimenthyl-1-(1,2,4-triazol-1-yl)-butan-2-one initially with bromine to form 1-bromo-(1,2,4-triazol-1-yl)-3,3-dimethyl-butan-2-one, and subsequently reaching this with 4-hydroxybenzaldehyde O-methyl oxime ether in the presence of a base. This synthesis can be illustrated by means of formulae as follows:

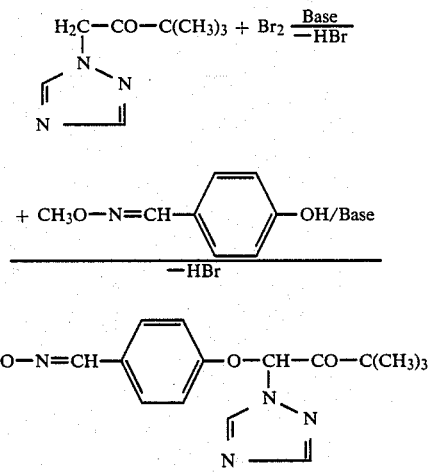

The process according to the invention is illustrated by the following example.

EXAMPLE 1

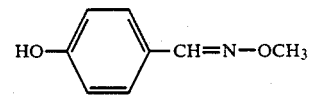

(I-1)

1st step

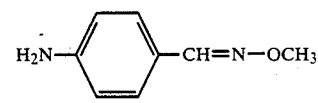

(III-1)

A solution of 45 g (0.25 mol) of 4-nitro-benzaldoxime O-methyl ether in 450 ml of tetrahydrofuran is introduced into a pressure vessel, and 7.5 g of Raney nickel are added. Hydrogen is introduced at room temperature until the theoretically calculated amount has been taken up. The hydrogen pressure is 3 bar. The reaction mixture is then worked up by filtering, and the filtrate remaining is evaporated by stripping off the solvent under reduced pressure. The residue is subjected to vacuum distillation. In this fashion, 38.1 g (95.2% of theory) of 4-amino-benzaldoxime O-methyl ether are obtained.

Boiling point: 105° C./0.1 mbar.

2nd step

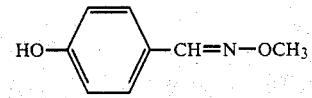

30 g (0.91 mol) of 4-amino-benzaldoxime O-methyl ether are slurried in 120 g of 25% strength aqueous sulphuric acid. The mixture is stirred for a further 30 minutes at room temperature and then cooled to 5°-10° C. A solution of 13.8 g (0.2 mol) of sodium nitrite in 80 ml of water is added dropwise to the reaction mixture within 30 minutes. The mixture is stirred for a further 1 hour at 5°-10° C., and the excess nitrite is subsequently destroyed by added urea. For hydrolysis, the diazonium solution is run rapidly into initially introduced aqueous sulphuric acid (120 g, 25% strength) at 80°-85° C., the temperature being kept constant. When the addition is complete, the mixture is stirred for a further 15 minutes at 80°-85° C. For work-up, the mixture is cooled to room temperature, the pH is adjusted to 5-6 using aqueous sodium hydroxide solution, and the product is extracted with methylene chloride. The organic phase is evaporated under reduced pressure. The crude product remaining is distilled in vacuo. 25.7 g (content according to GC: 95.4%; yield: 85% of theory) of 4-methoximinomethylphenol of boiling point 140°-142° C./0.13 mbar are obtained.

Preparation of the compound of the formula:

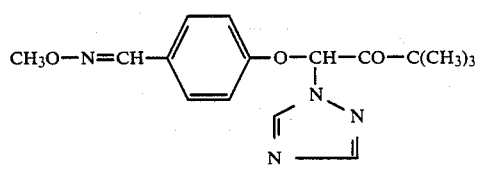

110 g (1.34 mols) of sodium acetate are introduced into a solution of 217 g (1.3 mols) of 3,3-dimethyl-1-(1,2,4-triazol-1-yl)-2-butanone in 700 ml of glacial acetic acid, the temperature increasing to about 28° C. The mixture is stirred for a further 30 minutes, and 208 g (1.3 mols) of bromine are added dropwise at 30° to 33° C. with slight cooling. The reaction mixture is stirred at room temperature for a further 2.5 hours and poured into 1,200 ml of water. The mixture is extracted with methylene chloride, and the extracts are washed with water and aqueous bicarbonate solution, dried over sodium sulphate and evaporated.

The crude 1-bromo-3,3-dimethyl-1-1(1,2,4-triazol1-yl)-2-butanone thus obtained is dissolved in 100 ml of acetonitrile and added to a slurry of 151 g (1 mol) of 4-methoximinomethylphenol and 150 g (1.09 mols) of potassium carbonate in 800 ml of acetonitrile, the temperature increasing to about 40° C. The reaction mixture is stirred for a further 3 hours at 60° to 65° C., subsequently cooled and poured into water. The mixture is extracted with toluene, and the extracts are washed with water, dried and evaporated. The residue is triturated in ligroin and dried on clay. 241 g (76% of theory) of 3,3-dimethyl-1-(4-mehtoximinomethyl-phenoxy)-1-(1,2,4-triazol-1-yl)butan-2-one of melting point 83°–87° C. are obtained.

EXAMPLE 2

The compound of the formula (I-2), which is shown below, has been prepared according to the process described in Example 1.

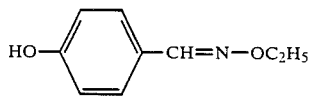
(I-2)

Melting point: 64° C.

It will be understood that the specification and examples are illustrative but not limitative of the present invention and that other embodiments within the spirit and scope of the invention will suggest themselves to those skilled in the art.

What is claimed is:

1. A process for the preparation of a hydroxy-benzaldoxime O-ether of the formula

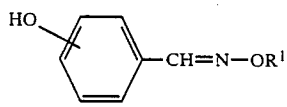
(I)

in which $R^1$ represents alkyl, comprising (a) in a first step, hydrogenating a nitro-benzaldoxime O-ether of the formula

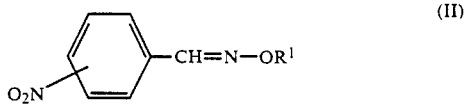
(II)

using the calculated amount of hydrogen in the presence of a catalyst and in the presence of a diluent, and (b) in a second step, reacting the amino-benzaldoxime O-ether of the formula

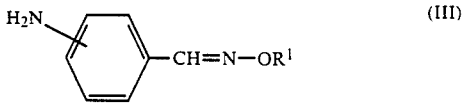
(III)

thus obtained with a diazotizing agent in acidic, aqueous solution, and, without isolation, thermally hydrolyzing the resultant diazonium salt of the formula

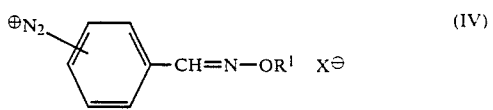
(IV)

in which $X^\ominus$ represents an equivalent of an inorganic anion,
in acidic, aqueous solution.

2. A process according to claim 1, in which $R^1$ is alkyl having 1 to 20 carbon atoms.

3. A process according to claim 1, in which $R^1$ is alkyl having 1 to 10 carbon atoms.

4. A process according to claim 1, in which $R^1$ is alkyl having 1 to 4 carbon atoms.

5. A process according to claim 1, wherein the starting material is 4-nitrobenzaldoxime O-methyl ether.

6. A process according to claim 1, wherein the hydrogenation catalyst is nickel-containing.

7. A process according to claim 1, wherein the diazotizing agent is sodium nitrite, potassium nitrite, ammonium nitrite or nitrosylsulphuric acid.

8. A process according to claim 1, wherein the acid in step (b) is sulphuric acid.

9. A process according to claim 1, wherein step (a) is carried out at a temperature between 0° C. and 100° C.

10. A process according to claim 1, wherein in step (b) the diazotization is carried out at a temperature between 0° C. and 20° C. and the thermal hydrolysis is carried out at a temperature between 50° C. and 100° C.

* * * * *